United States Patent
Jiang et al.

(10) Patent No.: US 10,786,370 B2
(45) Date of Patent: Sep. 29, 2020

(54) CARTILAGE REPAIR IMPLANT, AUXILIARY SURGICAL TOOL KIT AND CARTILAGE REPAIR SYSTEM

(71) Applicants: Industrial Technology Research Institute, Hsinchu (TW); National Taiwan University Hospital, Taipei (TW)

(72) Inventors: Ching-Chuan Jiang, Taipei (TW); Fang-Jie Jang, Keelung (TW); Ming-Chia Yang, Taipei (TW); Yun-Han Lin, Taichung (TW)

(73) Assignees: Industrial Technology Research Institute, Hsinchu (TW); National Taiwan University Hospital, Taipei (TW)

( * ) Notice: Subject to any disclaimer, the term of this patent is extended or adjusted under 35 U.S.C. 154(b) by 174 days.

(21) Appl. No.: 15/856,075

(22) Filed: Dec. 28, 2017

(65) Prior Publication Data
US 2019/0201203 A1    Jul. 4, 2019

(51) Int. Cl.
*A61F 2/46* (2006.01)
*A61F 2/30* (2006.01)

(52) U.S. Cl.
CPC .. *A61F 2/4618* (2013.01); *A61F 2002/30062* (2013.01); *A61F 2002/30751* (2013.01); *A61F 2002/30766* (2013.01)

(58) Field of Classification Search
CPC .............. A61F 2/30749; A61F 2/30756; A61F 2/4618; A61F 2002/30751;
(Continued)

(56) References Cited

U.S. PATENT DOCUMENTS 4,932,973 A * 6/1990 Gendler ..................... A61F 2/28
623/23.63
5,749,874 A * 5/1998 Schwartz ............ A61F 2/30749
606/215
(Continued)

FOREIGN PATENT DOCUMENTS

CN         101166485         4/2008
CN         101332313         12/2008
(Continued)

OTHER PUBLICATIONS

Office Action of Taiwan Counterpart Application, dated Aug. 8, 2018, pp. 1-3.
(Continued)

*Primary Examiner* — Eric S Gibson
(74) *Attorney, Agent, or Firm* — JCIPRNET

(57) ABSTRACT

A cartilage repair implant, an auxiliary surgical tool kit and a cartilage repair system are provided. The cartilage repair implant includes a body and a plurality of pins. The body is a porous structure and is configured to carry cartilage repair material. The pins are fixed to the body for being inserted into a patient's bone. The auxiliary surgical tool kit includes a positioning sleeve and a click tool. The positioning sleeve has a through passage. A first alignment structure is disposed on the sidewall of the through passage. The click tool includes an outer tube and a push rod. A second alignment structure mutually aligned with the first alignment structure is disposed on the outer wall of the outer tube. The outer tube is configured to pass through the through passage. The push rod is slidably disposed in the outer tube. One end of the outer tube has a shaping blade for slicing a to-be-implanted region on an affected area of the patient. In which the shape of the to-be-implanted region is corresponding to the shape of the body.

15 Claims, 11 Drawing Sheets
(2 of 11 Drawing Sheet(s) Filed in Color)

(58) Field of Classification Search
CPC ... A61F 2002/30766; A61F 2002/4627; C08L 29/04; C08L 68/04
See application file for complete search history.

(56) References Cited

U.S. PATENT DOCUMENTS

| | | | |
|---|---|---|---|
| 5,769,899 A | 6/1998 | Schwartz et al. | |
| 6,251,143 B1* | 6/2001 | Schwartz | A61B 17/064 606/75 |
| 6,267,772 B1* | 7/2001 | Mulhauser | A61F 2/0063 606/151 |
| 6,468,314 B2 | 10/2002 | Schwartz et al. | |
| 6,858,042 B2* | 2/2005 | Nadler | A61F 2/28 424/423 |
| 7,166,133 B2* | 1/2007 | Evans | A61L 27/12 623/23.51 |
| 7,361,195 B2 | 4/2008 | Schwartz et al. | |
| 7,837,740 B2 | 11/2010 | Semler et al. | |
| 8,012,205 B2* | 9/2011 | Plouhar | A61B 17/064 623/13.17 |
| 8,137,354 B2 | 3/2012 | Stone | |
| 8,157,805 B2* | 4/2012 | Re | A61B 17/0642 606/86 R |
| 8,183,041 B2 | 5/2012 | Liao et al. | |
| 8,435,551 B2 | 5/2013 | Semler et al. | |
| 8,556,972 B2* | 10/2013 | Gordon | A61F 2/30756 623/16.11 |
| 8,597,352 B2 | 12/2013 | Schwartz | |
| 8,641,718 B2 | 2/2014 | Meridew | |
| 8,715,366 B2 | 5/2014 | Borden | |
| 9,066,802 B2* | 6/2015 | Mansmann | A61F 2/3872 |
| 9,289,302 B2* | 3/2016 | Thomas | A61F 2/30756 |
| 9,504,574 B2 | 11/2016 | Farrar et al. | |
| 2001/0039455 A1* | 11/2001 | Simon | A61B 17/1604 623/23.51 |
| 2003/0004578 A1* | 1/2003 | Brown | A61F 2/30749 623/23.72 |
| 2003/0083665 A1 | 5/2003 | Re et al. | |
| 2003/0100947 A1 | 5/2003 | Nadler et al. | |
| 2004/0138758 A1* | 7/2004 | Evans | A61L 27/12 623/23.51 |
| 2004/0175408 A1* | 9/2004 | Chun | A61F 2/08 424/426 |
| 2004/0181232 A1* | 9/2004 | Re | A61B 17/0642 606/86 R |
| 2006/0178748 A1* | 8/2006 | Dinger, III | A61B 17/1615 623/18.11 |
| 2006/0271201 A1* | 11/2006 | Kumar | A61L 27/12 623/23.5 |
| 2007/0148242 A1 | 6/2007 | Vilei et al. | |
| 2008/0077251 A1 | 3/2008 | Chen et al. | |
| 2008/0119947 A1 | 5/2008 | Huckle et al. | |
| 2008/0167716 A1* | 7/2008 | Schwartz | A61F 2/0063 623/11.11 |
| 2008/0262616 A1 | 10/2008 | McKay | |
| 2009/0037148 A1* | 2/2009 | Lin | A61B 17/866 703/1 |
| 2009/0062821 A1* | 3/2009 | Johnson | A61F 2/30756 606/151 |
| 2010/0049322 A1 | 2/2010 | McKay | |
| 2010/0161073 A1* | 6/2010 | Thomas | A61F 2/30756 623/23.5 |
| 2010/0268337 A1* | 10/2010 | Gordon | A61F 2/28 623/16.11 |
| 2013/0144400 A1* | 6/2013 | Day | A61F 2/02 623/23.72 |
| 2016/0200043 A1* | 7/2016 | Thian | A61F 2/3872 623/23.72 |
| 2016/0206432 A1* | 7/2016 | Roby | A61F 2/30756 |
| 2019/0117402 A1* | 4/2019 | Stevens | A61L 27/227 |
| 2019/0201203 A1* | 7/2019 | Jiang | C08L 29/04 |

FOREIGN PATENT DOCUMENTS

| | | |
|---|---|---|
| CN | 102125448 | 7/2011 |
| CN | 103841927 | 6/2014 |
| CN | 104023655 | 9/2014 |
| CN | 104363826 | 2/2015 |
| CN | 105708517 | 6/2016 |
| CN | 106714736 | 5/2017 |
| CN | 106974697 | 7/2017 |
| CN | 107072787 | 8/2017 |
| TW | I316860 | 11/2009 |
| TW | 201004599 | 2/2010 |
| WO | 2007007106 | 1/2007 |

OTHER PUBLICATIONS

Iwan Zein, et al., "Fused deposition modeling of novel scaffold architectures for tissue engineering applications," Biomaterials, vol. 23, No. 4, Feb. 2002, pp. 1169-1185.
Kazunori Masuoka, et al., "Tissue Engineering of Articular Cartilage With Autologous Cultured Adipose Tissue-Derived Stromal Cells Using Atelocollagen Honeycomb-Shaped Scaffold With a Membrane Sealing in Rabbits," Journal of Biomedical Materials Research Part B, vol. 79, No. 1, Oct. 2006, pp. 25-34.
Zhensheng Li, et al., "Chitosan-alginate as scaffolding material for cartilage tissue engineering," Journal of Biomedical Materials Research Part A, vol. 75, No. 2, Nov. 1, 2005, pp. 485-493.
Hyeon Joo Kim, et al., "Bone tissue engineering with premineralized silk scaffolds," Bone, vol. 42, No. 6, Jun. 19, 2008, pp. 1226-1234.
Jessica M. Williams, et al., "Bone tissue engineering using polycaprolactone scaffolds fabricated via selective laser sintering," Biomaterials, vol. 26, No. 23, Aug. 2005, pp. 4817-4827.
Patricia B. Malafaya, et al., "Natural-origin polymers as carriers and scaffolds for biomolecules and cell delivery in tissue engineering applications," Advanced Drug Delivery Reviews, vol. 59, No. 4-5, May 30, 2007, pp. 207-233.
Ana Rita Costa-Pinto, et al., "Adhesion, Proliferation, and Osteogenic Differentiation of a Mouse Mesenchymal Stem Cell Line (BMC9) Seeded on Novel Melt-Based Chitosan/Polyester 3D Porous Scaffolds," Tissue Engineering: Part A, vol. 14, No. 6, Jun. 2008, pp. 1049-1057.
Lonnie D. Shea, et al., "Engineered Bone Development from a Pre-Osteoblast Cell Line on Three-Dimensional Scaffolds," Tissue Engineering, vol. 6, No. 6, Dec. 2000, pp. 605-617.
H. Yoshimoto, et al., "A biodegradable nanofiber scaffold by electrospinning and its potential for bone tissue engineering," Biomaterials, vol. 24, No. 12, May 2003, pp. 2077-2082.
"Office Action of China Counterpart Application", dated Jul. 1, 2020, p. 1-p. 10.

* cited by examiner

CARTILAGE REPAIR IMPLANT, AUXILIARY SURGICAL TOOL KIT AND CARTILAGE REPAIR SYSTEM

TECHNICAL FIELD

The disclosure relates to an implant, an auxiliary tool kit, and a system, and more specifically relates to a cartilage repair implant, an auxiliary surgical tool kit, and a cartilage repair system.

BACKGROUND

The articular cartilage is located on the surface layer of the bone at the knee and is a quite special tissue with multi-function in human body, in which the main functions of the articular cartilage is transferring stress in different directions of the upper and lower bone of the knee joint, absorbing the impact force transmitted to the articular surface from the bone, providing lubricating articular surface with low friction coefficient, and cooperating with the muscle ligament tissues, so as to perform sliding and rolling movement in different directions for knee joint activities.

The self-repair and regeneration capacities of cartilage tissue are very inadequate, and once cartilage tissue is damaged, it is often impossible to restore itself. According to statistics, at present, more than 200,000 cases of artificial knee joint replacement surgery are required in the United States each year because of deep cartilage injury, and the number of cases is still rising year by year. However, replacement of artificial knee joints requires removal of a large amount of cartilage and bone tissue from the patient's articular surface. The injuries and destructive effects are considerable. After the metal artificial knee joint is implanted in the body, the function of the metal artificial knee joint can only be maintained for about ten to fifteen years. In the case of young patients, they will face the pain of another artificial joint replacement surgery, but for elderly patients, they may not withstand to replace the artificial joint again. Furthermore, repeated replacement of artificial joints is likely to cause disability and poor performance, which further causes a heavy burden on society and families.

At present, for the medical treatment of cartilage damage, cartilage transplantation is mainly used to repair the damaged cartilage block. This method is a novel medical treatment invented in nearly 20 years, which includes autologous chondrocyte implantation (ACT) and osteoarticular allograft (OA). That is, autologous or allogeneic cartilage transplantation is adopted to regenerate new tissue, so as to avoid permanent destruction to the replaced artificial joint and thus avoid regular surgery to replace the aged metal or plastic components. Among the above treatment methods, autologous chondrocyte implantation is widely accepted because the source of the implanting tissues is the patient's own tissue, and there is no problems of allograft or xenograft transplantation immunological rejection.

The main stream of autologous transplantation is "Mosaic plasty procedure", which is a method proposed by a Hungarian surgeon in 1995. In this method, the cartilage at the stress-free surface of the patient's knee joint is drilled by a trepan to take a block having cartilage and a cylindrical bone plug contacting the bottom of cartilage, the same trepan is used to drill a recess having the same diameter at the damaged area, and the recess is filled with the block of undamaged and healthy cartilage and bone. However, in repairing cartilage wound by Mosaic plasty procedure, the cartilage surface between the implanted cartilage blocks has a tile interface, and the cartilage cells between the interfaces has a poor ability to divide because which is covered by a large amount of matrix. Therefore, it is actually not easy to form regenerative fusion between the cartilage blocks. On the other hand, fibrous cartilage tissue is generated in the gap at the periphery of cartilage block, which will make the wounded surface susceptible to osteoarthritis in the future.

Currently, the same problems also occur in the cartilage tissue cultured in vitro by tissue engineering to repair cartilage damage, and, after the cartilage tissue cultured in vitro is implanted to the wounded surface of cartilage, the fusion at the gap between the new and the old cartilage tissues is still a problem that is difficult to break through so far. Therefore, how to overcome the tissue regenerative fusion between the implanted cartilage and the original cartilage (host) is an important and urgent clinical research topic in orthopedics.

SUMMARY

The disclosure provides a cartilage repair implant, an auxiliary surgical tool kit, and a cartilage repair system, which can improve the existing problems of the conventional cartilage repair surgery.

A cartilage repair implant in one embodiment of the disclosure includes a body and a plurality of pins. The body is a porous structure and is configured to carry a cartilage repair material. One end of each of the pins is fixed to the body, and another end of each of the pins is configured to insert into a bone of a patient.

An auxiliary surgical tool kit in one embodiment of the disclosure includes a positioning sleeve and a click tool. The positioning sleeve has a through passage. A first alignment structure is disposed on the sidewall of the through passage. The click tool includes an outer tube and a push rod. A second alignment structure is disposed on the outer wall of the outer tube. The outer tube is configured to pass through the through passage of the positioning sleeve. The second alignment structure is mutually aligned with the first alignment structure. The push rod is slidably disposed in the outer tube. One end of the outer tube has a shaping blade for slicing a to-be-implanted region on an affected area of the patient.

A cartilage repair system in one embodiment of the disclosure includes a cartilage repair implant, a positioning sleeve, and a click tool. The cartilage repair implant includes a body and a plurality of pins. The body is a porous structure and is configured to carry a cartilage repair material. One end of each of the pins is fixed to the body, and another end of each of the pins is configured to insert into a bone of a patient. The positioning sleeve has a through passage. A first alignment structure is disposed on the sidewall of the through passage. The click tool includes an outer tube and a push rod. A second alignment structure is disposed on the outer wall of the outer tube. The outer tube is configured to pass through the through passage of the positioning sleeve. The second alignment structure is mutually aligned with the first alignment structure. The push rod is slidably disposed in the outer tube. One end of the outer tube has a shaping blade for slicing a to-be-implanted region on an affected area of the patient. The shape of the to-be-implanted region is corresponding to the shape of the body.

Based on the above, in the cartilage repair implant, the auxiliary surgical tool kit, and the cartilage repair system of the disclosure, the cartilage repair implant has a porous structure to assist in fusion at the gap between the new and the old cartilage tissues, and the auxiliary surgical tool kit helps the cartilage repair implant to be easily implanted to the affected area of the patient.

In order to make the aforementioned and other features and advantages of the disclosure more comprehensible, embodiments accompanying figures are described in detail bellows.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF DISCLOSED EMBODIMENTS

An auxiliary surgical tool kit in one embodiment of the disclosure includes a positioning sleeve and a click tool. Moreover, a cartilage repair system in one embodiment of the disclosure further includes a cartilage repair implant in addition to the aforementioned auxiliary surgical tool kit.

Figure 1:
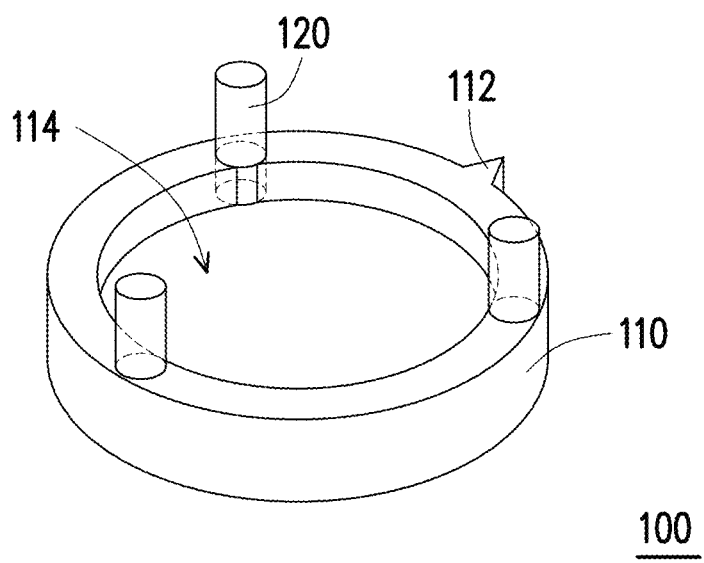
FIG. 1 is a schematic view of a cartilage repair implant of one embodiment of the disclosure.
Figure 2:
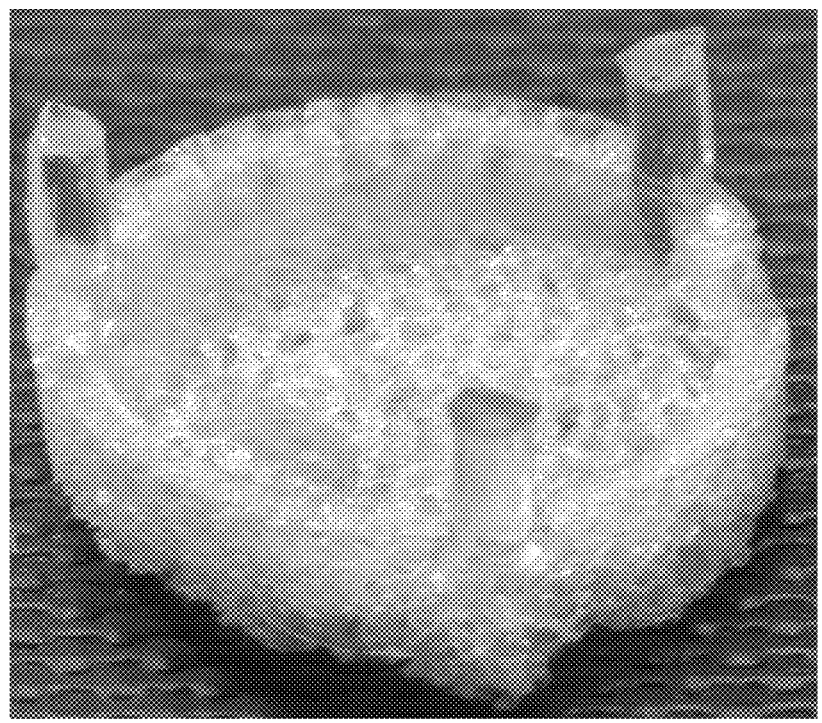
FIG. 2 is an actual photograph of a cartilage repair implant of one embodiment of the disclosure.

FIG. 1 is a schematic view of a cartilage repair implant of one embodiment of the disclosure, and FIG. 2 is an actual photograph of a cartilage repair implant of one embodiment of the disclosure. Referring to FIG. 1 and FIG. 2 simultaneously, in one embodiment, a cartilage repair implant 100 includes a body 110 and a plurality of pins 120. The body 110 is a porous structure and is configured to carry a cartilage repair material. The pins 120 are solid structures, one end of each of the pins 120 is fixed to the body 110, and another end of each of the pins 120 is configured to insert into the bone of the patient during surgery in order to fix the entire cartilage repair implant 100 to the patient's bone. Alternatively, the body 110 of the present embodiment can further has a recess 114, in which the space of the recess 114 can be provided to carry the materials used to repair the cartilage.

In one embodiment, a porous structure may be adopted to be the body 110 of the cartilage repair implant 100, so as to allow adjacent tissues or cells and lubricating fluid to penetrate the pores to enter the interior of the body 110 or the space of the recess 114 for repairing the affected area together with the cartilage repair materials, thereby improving the recovery effect.

In one embodiment, biodegradable material may be adopted to be the material of the body 110. Accordingly, after the affected area of the patient is completely repaired, the cartilage repair implant 100 can be naturally decomposed and metabolized in the patient's body. In addition, only the normal cartilage that has been recovered to function will be left without leaving any non-natural human element/part in the patient's body. In one embodiment, the material of the body 110 may be one single type of biodegradable material, such material composition is relatively simple, so as to further shorten the time required for complete degradation. In one embodiment, the material of the body 110 may be a single polymer material, such as Polylactide (PLA), Polyglycolic Acid (PGA), Polycaprolactone (PCL), Polyvinyl alcohol (PVA), polyhydroxy-alkanoates (PHA), but not be limited thereto. In another embodiment, the material of the body 110 may be composite polymer materials, such as a co-polymer of at least two of the aforementioned polymers, but not be limited thereto.

In one embodiment, biodegradable material may be adopted to be material of the pins 120. In one embodiment, the material of the pins 120 may be one single type of biodegradable material, such material composition is relatively simple, so as to further shorten the time required for complete degradation. In one embodiment, the material of the pins 120 may be a single polymer material, such as Polylactide (PLA), Polyglycolic Acid (PGA), Polycaprolactone (PCL), Polyvinyl alcohol (PVA), polyhydroxy-alkanoates (PHA), but not be limited thereto. In another embodiment, the material of the pins 120 may be composite polymer materials, such as a co-polymer of at least two of the aforementioned polymers, but not be limited thereto. Moreover, the material of the body 110 and the material of the pins 120 may be the same or different.

In one embodiment, the porosity of the porous structure of the body 110 is ranging from 50% to 90%, such as 50%, 55%, 60%, 65%, 70%, 75%, 80%, 85%, or 90%. Moreover, the size of the pore of the porous structure is about 50 μm to 1,000 μm. In one embodiment, the appearance of the body 110 may be a disc or a shell, but not be limited thereto. In one embodiment, the diameter of the body 110 may be ranging from about 8 mm to 10 mm, and can be applied to the cartilage having different degrees of defect. The wall thickness of the body 110 may be ranging from 1 mm to 1.5 mm and has sufficient strength to resist the compressive force of the surrounding tissue, so as not be compressed to invade the space of storing the cartilage repair material. The total height of the body 110 may be ranging from about 1.8 mm to 2.2 mm and is substantially the same as the thickness of the cartilage layer of human knee, so that the body 110 does not harm the bone during surgical operation and the body 110 does not protrude from the surface of the knee joint after the surgery, so as to avoid being worn away by the articular surface. In one embodiment, the diameter of the pins 120 may be ranging from 1 mm to 2 mm, and the length of the pins 120 may be ranging from 2 mm to 3 mm. In addition, each of the pins 120 may be a solid column, so as to fix the body 110 to the damaged region of the cartilage in a manner of minimum destruction for the bones.

In one embodiment, the periphery of the body 110 has a positioning protruding 112. The positioning protruding 112 may be a small sharp tip protruding about 0.5 mm to 1 mm, such as a protrusion having an appearance of a triangle, but not be limited thereto. The positioning protruding 112 may be used with the positioning structures of other surgical instruments together, so as to assist in positioning and guiding the cartilage repair implant 100 to the correct position during the surgical operation.

Figure 3:
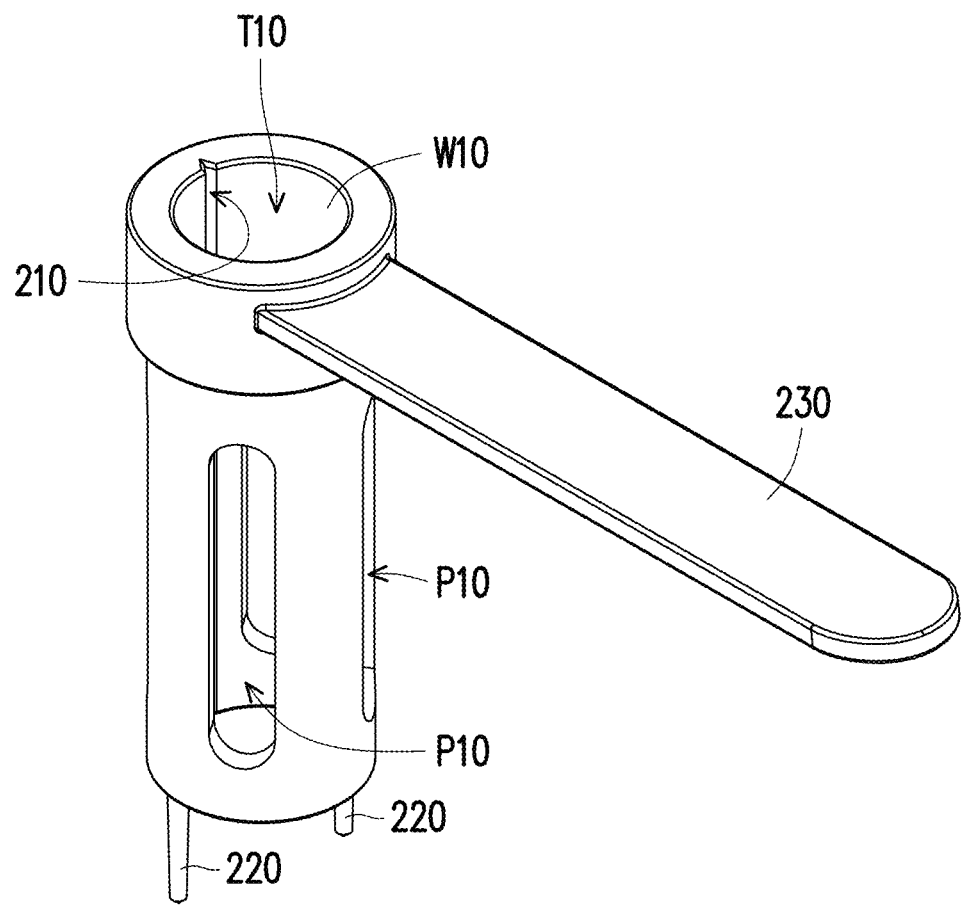
FIG. 3 is a schematic view of a positioning sleeve of an auxiliary surgical tool kit of one embodiment of the disclosure.
Figure 4A:
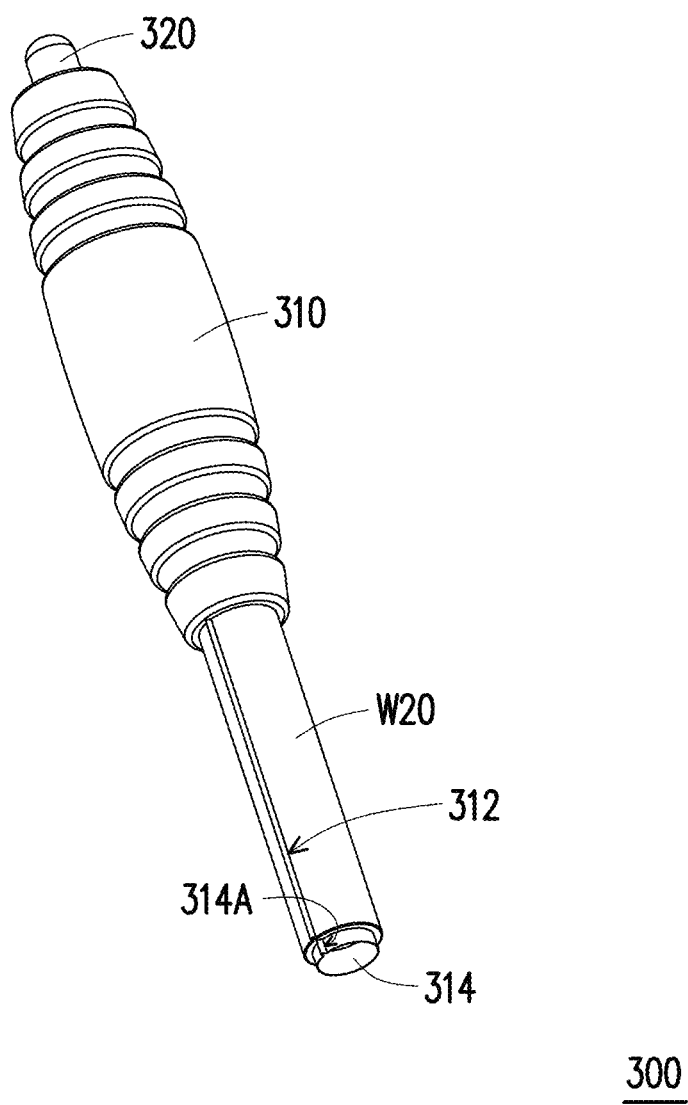
FIG. 4A and FIG. 4B respectively are a schematic view of appearance and a cross-sectional schematic view of a click tool of an auxiliary surgical tool kit of one embodiment of the disclosure.
Figure 4B:
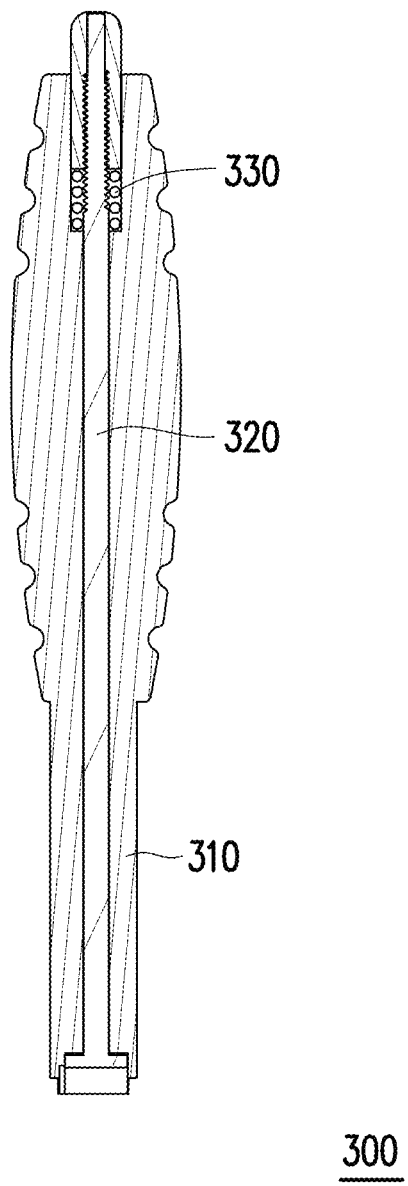

FIG. 3 is a schematic view of a positioning sleeve of an auxiliary surgical tool kit of one embodiment of the disclosure. Referring to FIG. 3, a positioning sleeve 200 has a through passage T10. A first alignment structure 210 is disposed on the sidewall W10 of the through passage T10. FIG. 4A and FIG. 4B respectively are a schematic view of appearance and a cross-sectional schematic view of a click tool of an auxiliary surgical tool kit of one embodiment of the disclosure. Referring to FIG. 4A and FIG. 4B, the click tool 300 includes an outer tube 310 and a push rod 320. A second alignment structure 312 is disposed on the outer wall W20 of the outer tube 310. The outer tube 310 is configured to pass through the through passage T10 of the positioning sleeve 200 in FIG. 3. The second alignment structure 312 is mutually aligned with the first alignment structure 210 in FIG. 3, so as to ensure the click tool 300 is accurately positioned with the positioning sleeve 200 during operation. The push rod 320 may be slidably disposed in the outer tube 310 and can slide inside the outer tube 310 by pressing or pushing. One end of the outer tube 310 has a shaping blade 314 for slicing a to-be-implanted region (not illustrated) on the affected area of the patient. The shape of the to-be-implanted region may be corresponding to the shape of the body 110 in FIG. 1.

Referring to FIG. 3, FIG. 4A, and FIG. 4B, when the outer tube 310 of the click tool 300 is performed to pass through the through passage T10 of the positioning sleeve 200, since the first alignment structure 210 is disposed in the positioning sleeve 200 and the second alignment structure 312 is disposed on the outer wall W20 of the outer tube 310 of the click tool 300, and the second alignment structure 312 must be mutually aligned with the first alignment structure 210, so as to limit the orientation of the click tool 300 when sliding. In addition, one end away from the shaping blade 314 of the slidable push rod 320 disposed inside the outer tube 310 is disposed to protrude out of the outer tube 310. When the user pushes the end, which is disposed to protrude out of the outer tube 310, of the push rod 320, the push rod 320 can be pushed in a direction toward the shaping blade 314.

In one embodiment, the shape of the shaping blade 314 may be designed to match with the shape of the body 110 of the cartilage repair implant 100. That is, the shaping blade 314 is designed to have the same outline and configuration as the body 110 to completely accommodate the body 110, so that the cartilage repair implant 100 can be completely placed within the area that constructed by the shaping blade 314. As a result, the user can only need to simply push the push rod 320 to push the cartilage repair carrier 100 into a target at the affected area. In other words, in addition to slicing the to-be-implanted region by the shaping blade 314, the click tool 300 can further serve as a tool to push the cartilage repair implant 100 to the to-be-implanted region. In other embodiment, for convenience in use, an elastic restoring member 330, such as a spring, is disposed between the outer tube 310 and the push rod 320, so that the push rod 320 can be automatically reset.

Referring to FIG. 3, in one embodiment, one end of the positioning sleeve 200 has a plurality of sleeve pins 220 configured to insert into the affected area of the patient. Accordingly, during the surgical operation, the position of the positioning sleeve 200 is preliminarily fixed and the surgical site is preliminarily defined in order to accurately carry out the following surgery. The length of the sleeve pin 220 may be ranging from 8 mm to 12 mm, such as 10 mm, and the angle between the outer surface and the central axis of the sleeve pin 220 may be ranging from 0.5 to 2 degrees, such as 1 degree, so that, when the sleeve pins 220 is driven into the bone and to be fixed therein, the resistance can be reduced and it is easier to drive the sleeve pins 220 into the bone. The diameter of the through passage T10 may be ranging from 12 mm to 14 mm, such as 13 mm, so as to provide the space for operating the instruments in the following surgery. Moreover, at least one discharge opening P10 is disposed at the sidewall W10 of the through passage T10, such as two or three, but the disclosure is not limited thereto. In one embodiment, there are four discharge openings P10. The discharge opening P10 may be a rectangular opening having a width of 1-5 mm and a length of 20-30 mm, such as a rectangular opening having a width of 2.5 mm and a length of 24 mm to 25 mm. When using a debridement drill to perform debridement in the following process, the tissue is removed and then discharged through the discharge openings P10, so as to make the wound clean.

Additionally, in yet another embodiment, another end, which is opposite to the end having the sleeve pins 220, of the aforementioned positioning sleeve 200 has a grip 230 configured to be held by an user, so as to improve the convenience in use. Moreover, the aforementioned first alignment structure 210 disposed on the sidewall W10 of the through passage T10 may have a guiding passage with a length of 0.5-2 mm, such as 1 mm, configured to provide alignment function for other surgical instruments, so as to ensure that a plurality of the pins 120 of the cartilage repair implant 100 can be smoothly inserted into and tightly pressed into the small holes in the bone.

Referring to FIG. 1 and FIG. 4A simultaneously, in one embodiment, a positioning protruding 314A is disposed at the shaping blade 314. The positioning protruding 314A of the shaping blade 314 and the positioning protruding 112 of the cartilage repair implant 100 can be mutually aligned with each other. Therefore, when the cartilage repair implant 100 is disposed within the area encircled by the shaping blade 314, it can be ensured that the cartilage repair implant 100 is disposed in proper orientation for the subsequent operation.

Figure 5:
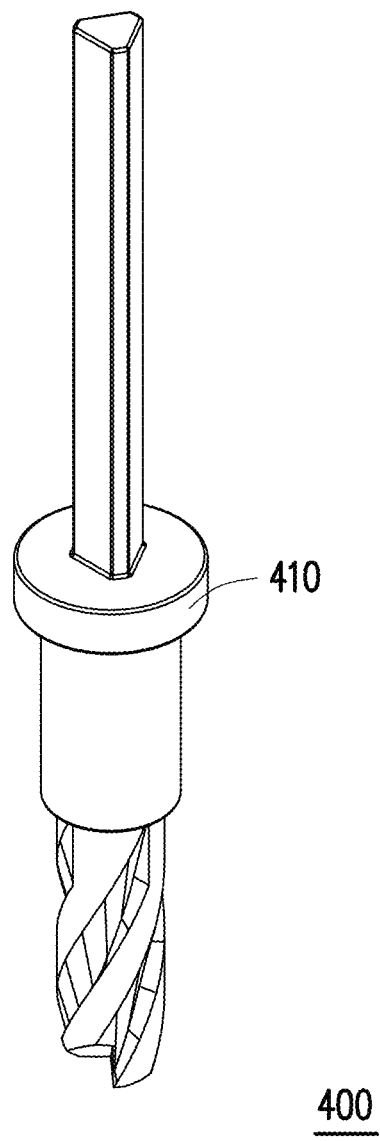
FIG. 5 is a schematic view of a debridement drill of an auxiliary surgical tool kit of one embodiment of the disclosure.

FIG. 5 is a schematic view of a debridement drill of an auxiliary surgical tool kit of one embodiment of the disclosure. Referring to FIG. 3 and FIG. 5 simultaneously, in one embodiment, a debridement drill 400 can pass through the through passage T10 of the positioning sleeve 200 to remove cartilage at the to-be-implanted region of the patient, so as to vacate a space in the affected area of the patient for implanting the cartilage repair implant 100 shown in FIG. 1. In another embodiment, the debridement drill 400 has a stop portion 410. The size of the stop portion 410 is greater than the size of the through passage T10. In one embodiment, the diameter of the stop portion 410 is about 14-16 mm, such as 15 mm. Therefore, when the debridement drill 400 is performed to pass through the through passage T10 of the positioning sleeve 200, the stop portion 410 does not allow the debridement drill 400 to continue moving forward, so as to limit the debriding depth of the debridement drill 400. For example, the stop portion 410 allows the debridement drill 400 to protrude from the positioning sleeve 200 a distance of 2 mm, so the depth of the cartilage removed by the debridement drill 400 is also 2 mm. In other words, the depth of the cartilage removed by the debridement drill 400 is equal to the height of the body 110 of the cartilage repair implant 100.

In another embodiment, the diameter of the drilling portion at the bottom of the debridement drill 400 is about 8 to 10 mm, which is designed to fit the diameter of the body 110 of the cartilage repair implant 100. More specifically, the diameter of the drilling portion at the bottom of the debridement drill 400 is substantially equal to the outer diameter of the body 110 of the cartilage repair implant 100 to clear out the space suitable for accommodation of the cartilage repair implant 100. Since the debridement drill 400 is designed to rotate inside the through passage T10, there is no structure disposed on the debridement drill 400 corresponding to the first alignment structure 210 of the through passage T10.

Figure 6:
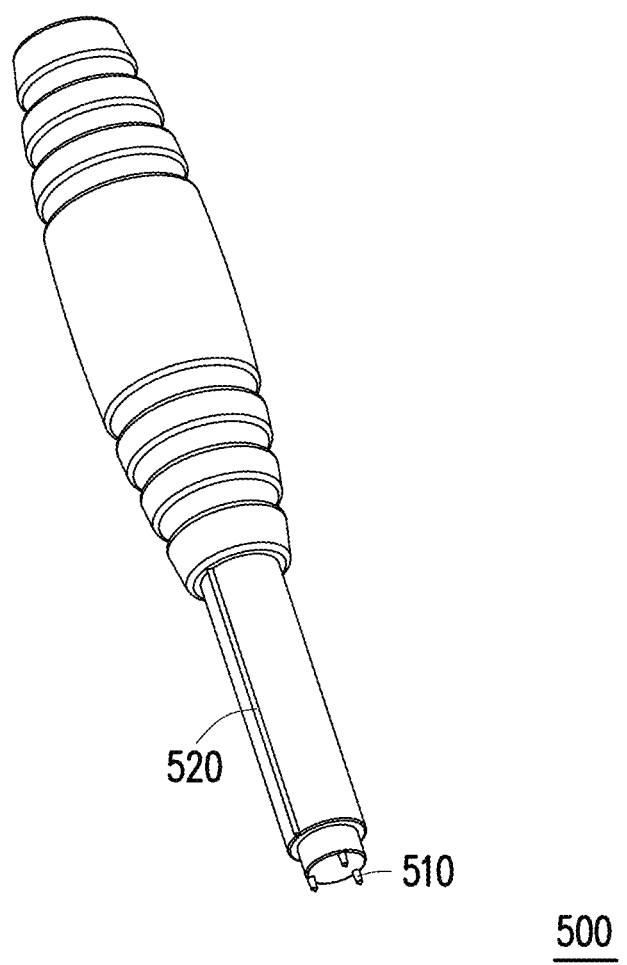
FIG. 6 is a schematic view of a drilling instrument of an auxiliary surgical tool kit of one embodiment of the disclosure.

FIG. 6 is a schematic view of a drilling instrument of an auxiliary surgical tool kit of one embodiment of the disclosure. Referring to FIG. 3 and FIG. 6 simultaneously, the drilling instrument 500 of the present embodiment is configured to pass through the through passage T10 of the positioning sleeve 200 and drill a plurality of positioning holes in cartilage located at the to-be-implanted region of the patient (not shown). For example, the drilling instrument 500 has a plurality of pins 510, and the locations of the positioning holes drilled by the pins 510 may be corresponding to the locations of the pins 120 of the cartilage repair implant 100. That is, if the number of the pins 120 is three, the positioning angles of the three pins 120 with respect to the central axis of the drilling instrument 500 are 0 degree, 120 degrees, and 240 degrees. That is, the three pins 120 are distributed in point symmetry manner. The angle between the outer surface and the central axis of the pin 120 is, for example, ranging from 3 degrees to 5 degrees, so as to drill the positioning holes that are inclined. To be more specific, because the positioning holes are inclined, the deeper the pins 120 of the cartilage repair implant 100 are inserted into the positioning holes, the tighter the positioning holes can hold the pins 120, so that the cartilage repair implant 100 is firmly fixed to the affected area of the patient.

Moreover, in another embodiment, the drilling instrument 500, for example, has a third alignment structure 520, and the third alignment structure 520 is mutually aligned with the first alignment structure 210 in FIG. 3. Therefore, the orientation of the drilling instrument 500 is limited when sliding inside the outer tube 310, so as to ensure that the locations of the positioning holes drilled by the drilling instrument 500 are corresponding to the locations of the pins 120 of the cartilage repair implant 100 in the following implantation.

Figure 7A:
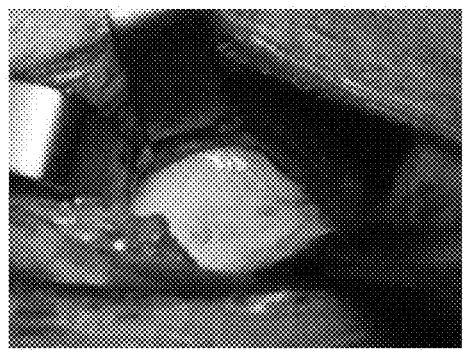
FIG. 7A to FIG. 7G are photographs of various stages of using a cartilage repair system of one embodiment of the disclosure to perform cartilage repair surgery.

FIG. 7A to FIG. 7G are photographs of various stages of using a cartilage repair system of one embodiment of the disclosure to perform cartilage repair surgery for a pig. Referring to FIG. 7A, a normal adult pig is adopted to be the object to perform a minimally invasive knee surgery. During the experiment, the identity number, the age, the weight, the gender, and the relevant information about surgery and anatomy are recorded. Each pig is fasted for 24 hours before surgery, anesthetic used in surgery is 3% sodium pentobarbital and is injected into the hind legs with a dose about equivalent to 1 mL/kg, and the dose of anesthetic is adjusted depending on the anesthesia condition of each pig. After confirming that the pigs have been anesthetized, the pigs are shaved and sterilized with iodine, and the outside of the surgical site is covered with a sterile towel to expose only the joint position, so as to ensure that the surgery is carried out under sterile condition. Subsequently, a wound of about 3 cm was cut on the lateral skin, and the soft tissue was peeled off to expose the location where the cartilage repair implant 100 shown in FIG. 1 was to be implanted.

Figure 7B:
Figure 7C:
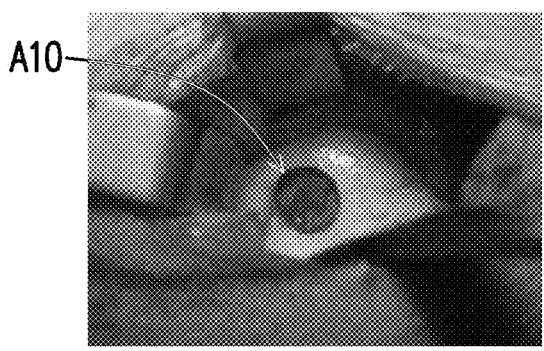

After that, referring to FIG. 7B, the positioning sleeve 200 shown in FIG. 3 is performed to place on the affected area, and the two sleeve pins 220 of the positioning sleeve 200 are performed to drive and fix to the affected area. Next, referring to FIG. 7C, the click tool 300 shown in FIG. 4 is performed to insert into the positioning sleeve 200 and the shaping blade 314 is performed to slice the to-be-implanted region A10 on the affected area. Subsequently, the debridement drill 400 shown in FIG. 5 is performed to insert into the positioning sleeve 200 to remove the cartilage at the to-be-implanted region A10.

Figure 7D:
Figure 7E:
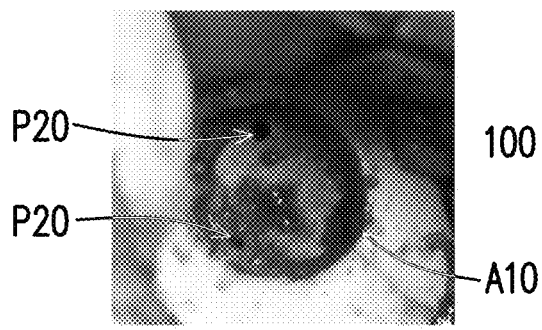
Figure 7F:
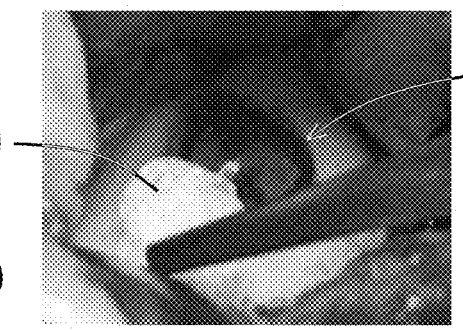
Figure 7G:
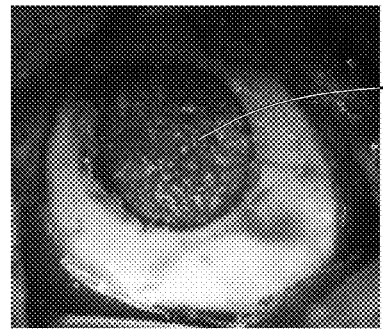

Next, referring to FIG. 7D, the drilling instrument 500 shown in FIG. 6 is performed to insert into the positioning sleeve 200 to drill a plurality of positioning holes P20 shown in FIG. 7E in the bone at the to-be-implanted region A10. Subsequently, referring to FIG. 7F, the cartilage repair implant 100 shown in FIG. 1 is performed to place at the to-be-implanted region A10. For better understanding, in FIG. 7F, the cartilage repair implant 100 is placed beside the to-be-implanted region A10, but the click tool 300 shown in FIG. 4A is used to push the cartilage repair implant 100 directly into the to-be-implanted region A10 in the actual surgery. Since the shape of the shaping blade 314 is corresponding to the shape of the cartilage repair implant 100 and there are positioning structures to align the drilling instrument 500 and the positioning sleeve 200, the locations of the positioning holes P20 drilled by the drilling instrument 500 are naturally corresponding to the pins 120 of the cartilage repair implant 100 without any additional alignment steps. Accordingly, not only the time required for surgery can be shorten, but also the chance of successful operation can be improved due to accurate alignment. FIG. 7G shows that the cartilage repair implant 100 is already placed into the to-be-implanted region A10.

Figure 8:
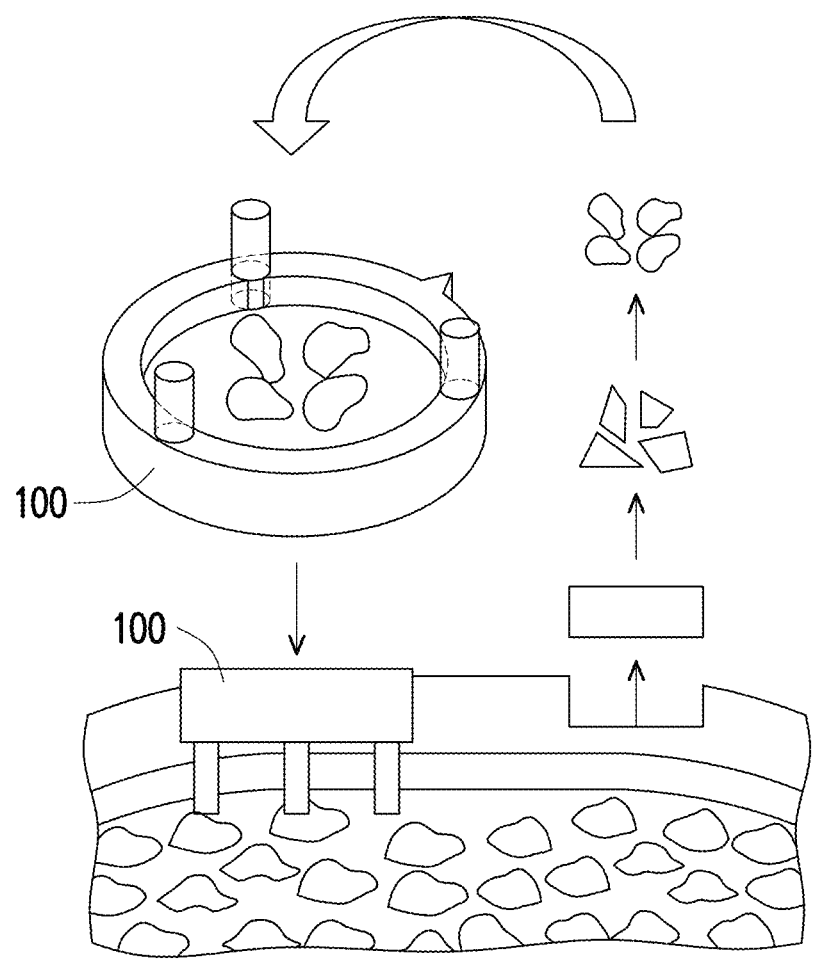
FIG. 8 is a schematic view showing a method for applying a cartilage repair implant of one embodiment of the disclosure.

FIG. 8 is a schematic view showing a method for applying a cartilage repair implant of one embodiment of the disclosure. Referring to FIG. 8, the cartilage repair material is taken from the patients themselves, and particularly from the cartilage at the non-stress place of the knee joint, such as scraping the autologous cartilage with a curette. After being scraped, the aforementioned autologous cartilage is placed in 10 cm Petri dish and then is chopped by a surgical knife/scalpel, the size of the pieces is controlled between 560-800 μm by a sieve with 20 to 40 mesh. The chopped pieces of cartilage are collected in 15 ml centrifuge tubes, are added with 5 ml of collagenase, and are placed in a 37° C. incubator for 1 hour standing for liberation of part of cartilage cells. In which, collagenase is prepared with phosphate-buffered saline (PBS), and is adjusted to have a ratio of 2 mg/ml PBS. After being dissolved and separated by collagenase, the cartilage pieces were transferred into a centrifuge and centrifuged with a speed of 1500 r.p.m. for 5 minutes, so as to further separate the collagenase from the cartilage pieces. After centrifugation, suction was performed to remove the collagenase supernatant, and the remaining cartilage pieces and the cell tissues were washed twice by PBS and centrifuged twice to remove the residual collagenase, so as to complete the preparation of the cartilage repair material.

Next, the aforementioned prepared cartilage repair material was transferred into a 1 c.c. syringe and then injected on the cartilage repair implant 100 through an 18 G needles. After that, the cartilage repair implant 100 is placed in a manner that the surface carrying the cartilage repair material faces towards the affected area, so that the cartilage repair material can be performed to contact the affected area directly. Otherwise, since the cartilage repair material has a certain viscosity, it is not easy for the cartilage repair material to drop from the cartilage repair implant 100.

Figure 9A:
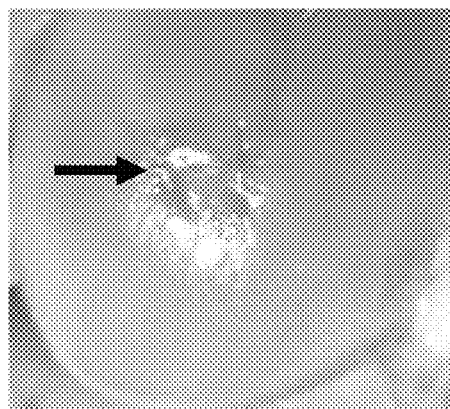
FIG. 9A and FIG. 9B respectively are photographs of affected areas recovered after 6 months of an experimental example of using a cartilage repair system of one embodiment of the disclosure to perform surgery and a comparative example using the conventional auxiliary surgical tool kit to perform the surgery.
Figure 9B:
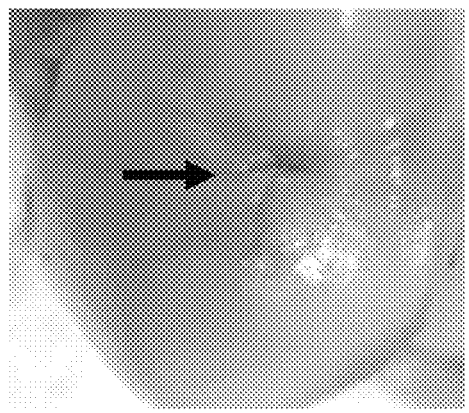

FIG. 9A and FIG. 9B respectively are photographs of affected areas after being recovered of an experimental example of using a cartilage repair system of one embodiment of the disclosure to perform surgery and a comparative example using the conventional auxiliary surgical tool kit to perform the surgery, and the surgical objects are all pigs as aforementioned. As shown in FIG. 9A, 12 months after using the auxiliary surgical tool kit of one embodiment of the disclosure to perform the surgery, the cartilage of the affected area (as indicated by the arrow) is well recovered with almost no visible trace of the wound. In contrast, 12 months after using the conventional auxiliary surgical tool kit to perform the surgery, the cartilage of the affected area (as indicated by the arrow in FIG. 9B) is poorly recovered and the traces of the wound are obvious.

Figure 10A:
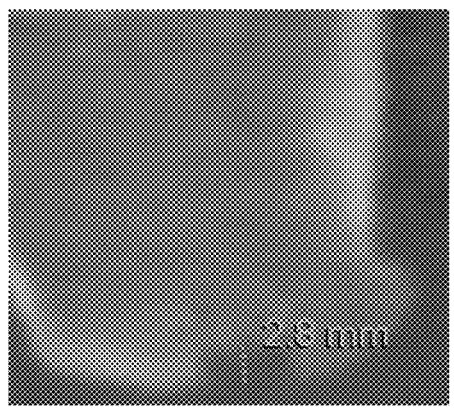
FIG. 10A and FIG. 10B respectively are X-ray films of affected areas recovered after 6 months of an experimental example of using a cartilage repair system of one embodiment of the disclosure to perform the surgery and a comparative example using the conventional auxiliary surgical tool kit to perform the surgery.
Figure 10B:
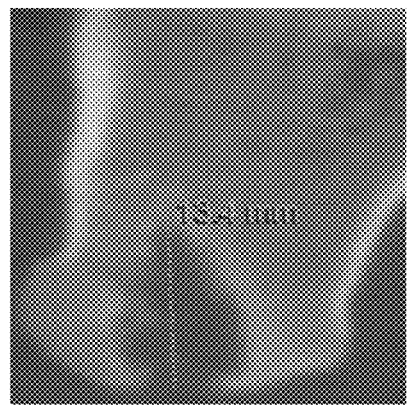

FIG. 10A and FIG. 10B respectively are X-ray films of affected areas recovered after 6 months of an experimental example of using a cartilage repair system of one embodiment of the disclosure to perform the surgery and a comparative example using the conventional auxiliary surgical tool kit to perform the surgery, and the surgical objects are all pigs as aforementioned. As shown in FIG. 10A, 6 months after using the auxiliary surgical tool kit of one embodiment of the disclosure to perform the surgery, the cartilage of the affected area is rapidly recovered, and the depth of the wound is only 2.8 mm. In contrast, 6 months after using conventional auxiliary surgical tool kit to perform the surgery, the cartilage of the affected area (as indicated by the arrow in FIG. 9B) is recovered slower and the depth of the wound is up to 13.4 mm.

Figure 11A:
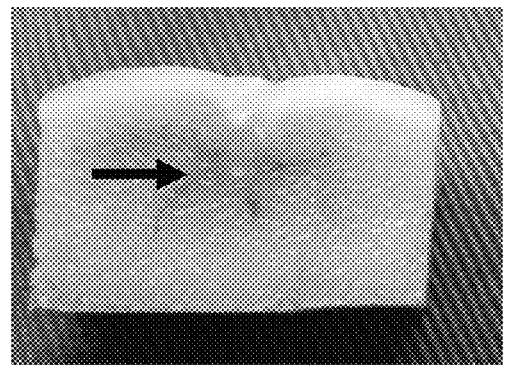
FIG. 11A and FIG. 11B respectively are sample photographs of affected areas recovered after 6 months of an experimental example of using a cartilage repair system of one embodiment of the disclosure to perform the surgery and a comparative example using the conventional auxiliary surgical tool kit to perform the surgery.
Figure 11B:
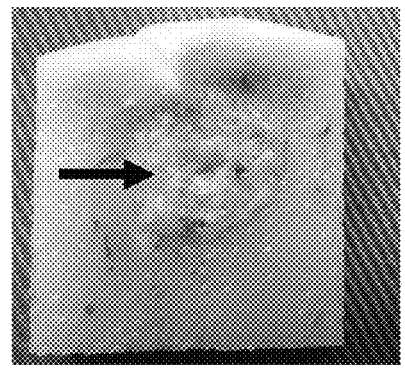

FIG. 11A and FIG. 11B respectively are sample photographs of affected areas recovered after 6 months of an experimental example of using a cartilage repair system of one embodiment of the disclosure to perform the surgery and a comparative example using the conventional auxiliary surgical tool kit to perform the surgery, and the surgical objects are all pigs as aforementioned. As shown in FIG. 11A, 6 months after using the auxiliary surgical tool kit of one embodiment of the disclosure to perform the surgery, the bone of the affected area (as indicated by the arrow) is rapidly recovered, only a few surgical residues are left and the cartilage thereof is well recovered. In contrast, 6 months after using conventional auxiliary surgical tool kit to perform the surgery, the bone of the affected area (as indicated by the arrow in FIG. 11B) is recovered slower and there are many surgical residues left.

Figure 12A:
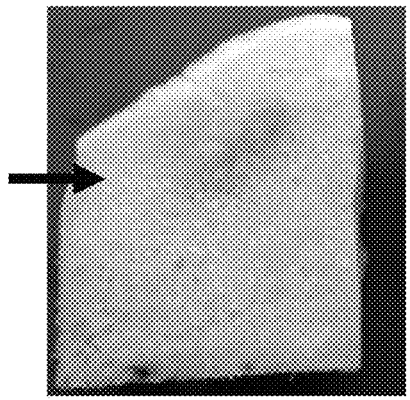
FIG. 12A and FIG. 12B respectively are sample photographs of affected areas recovered after 12 months of an experimental example of using a cartilage repair system of one embodiment of the disclosure to perform the surgery and a comparative example using the conventional auxiliary surgical tool kit to perform the surgery.
Figure 12B:
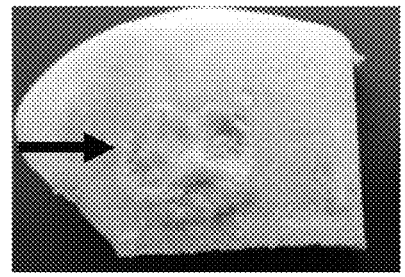

FIG. 12A and FIG. 12B respectively are sample photographs of affected areas recovered after 12 months of an experimental example of using a cartilage repair system of one embodiment of the disclosure to perform the surgery and a comparative example using the conventional auxiliary surgical tool kit to perform the surgery, and the surgical objects are all pigs as aforementioned. As shown in FIG. 12A, 12 months after using the auxiliary surgical tool kit of one embodiment of the disclosure to perform the surgery, the bone of the affected area (as indicated by the arrow) is well recovered, there is almost no surgical residues, and the newborn bone tissue has indeed grown therein. In contrast, 12 months after using the conventional auxiliary surgical tool kit to perform the surgery, the bone of the affected area (as indicated by the arrow in FIG. 12B) is poorly recovered and there are still many surgical residues left.

Figure 13A:
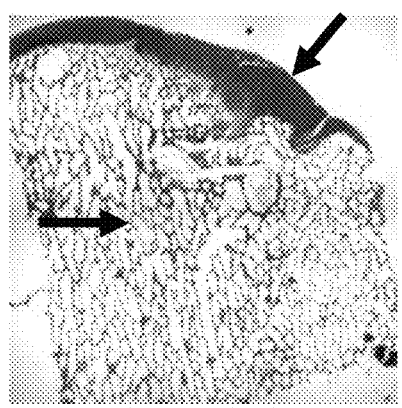
FIG. 13A and FIG. 13B respectively are staining slices of affected areas recovered after 12 months of an experimental example of using a cartilage repair system of one embodiment of the disclosure to perform the surgery and a comparative example using the conventional auxiliary surgical tool kit to perform the surgery.
Figure 13B:
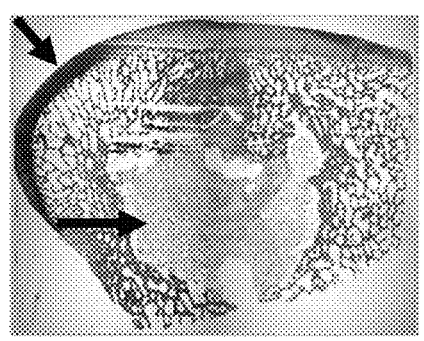

FIG. 13A and FIG. 13B respectively are staining slices of affected areas after being recovered of an experimental example of using a cartilage repair system of one embodiment of the disclosure to perform the surgery and a comparative example using the conventional auxiliary surgical tool kit to perform the surgery, and the surgical objects are all pigs as aforementioned. As shown in FIG. 13A and FIG. 13B, both of Safranin-O and Fast Green (FCF) are used simultaneously for dyeing, so as to further detect the status of cartilage hyperplasia and status of bone recovery.

Referring to FIG. 13A and FIG. 13B simultaneously, it can be known from the stained area of Safranin-O that 12 months after using the auxiliary surgical tool kit of one embodiment of the disclosure to perform the surgery, as indicated by the arrow at the top of FIG. 13A, the condition of cartilage hyperplasia is good. However, the condition of cartilage hyperplasia is just normal after using the conventional auxiliary surgical tool kit to perform the surgery, as indicated by the arrow at the top of FIG. 13B. On the other hand, it can be known from the stained area of FCF that the condition of bone recovery is good, as indicated by the arrow at the middle of FIG. 13A, 12 months after using the auxiliary surgical tool kit of one embodiment of the disclosure to perform the surgery. However, there is almost no bone hyperplasia, as indicated by the arrow at the middle of FIG. 13B, after using the conventional auxiliary surgical tool kit to perform the surgery.

Figure 14:
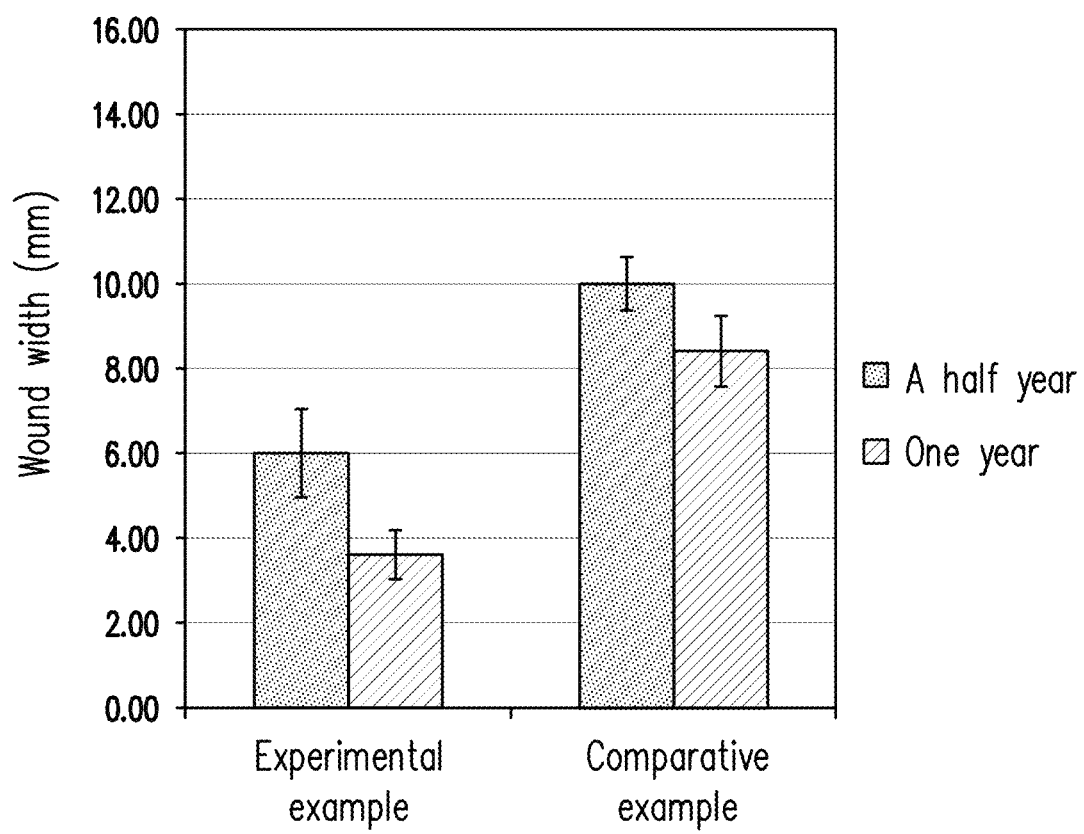
FIG. 14 is a quantitative diagram of wound widths of an experimental example of using a cartilage repair system of one embodiment of the disclosure to perform the surgery and a comparative example using the conventional auxiliary surgical tool kit to perform the surgery.

FIG. 14 is a quantitative diagram of wound widths of an experimental example of using a cartilage repair system of one embodiment of the disclosure to perform the surgery and a comparative example using the conventional auxiliary surgical tool kit to perform the surgery. Referring to FIG. 14, the wound width in the experimental example using the auxiliary surgical tool kit of one embodiment of the disclosure to perform the surgery is equal to 60% of the wound width of the comparative example using the conventional auxiliary surgical tool kit to perform the surgery after a half year, and the wound width in the experimental example is equal to 50% of the wound width of the comparative example after one year.

In summary, in the cartilage repair implant, the auxiliary surgical tool kit, and the cartilage repair system of the disclosure, the cartilage repair implant adopts a porous structure to assist in fusion at the gap between the new and the old cartilage tissues, and the auxiliary surgical tool kit makes the minimally invasive cartilage repair surgery possible. In addition, when biodegradable materials are adopted, the cartilage repair implant can carry cartilage repair material and cooperate with the positionable auxiliary surgical tool kit to accurately position and implant the cartilage repair implant to the affected area of the patient in a minimally invasive manner. In this way, it is possible to assist in reconstructing a cartilage defect site with less damage to the bone, and the cartilage repair implant can be naturally decomposed and metabolized in the patient's body after the repair is completed.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. An auxiliary surgical tool kit, comprising:
    a positioning sleeve, having a through passage, wherein a alignment groove is disposed on a sidewall of the through passage; and
    a click tool, comprising an outer tube and a push rod, wherein a first alignment protrusion is disposed on an outer wall of the outer tube, the outer tube is configured to pass through the through passage of the positioning sleeve, and the first alignment protrusion is mutually aligned with the alignment groove, the push rod is slidably disposed in the outer tube, one end of the outer tube has a shaping blade configured to slice a to-be-implanted region on an affected area of a patient.

2. The auxiliary surgical tool kit as recited in claim 1, wherein one end of the positioning sleeve has a plurality of sleeve pins configured to be inserted into the affected area of the patient.

3. The auxiliary surgical tool kit as recited in claim 2, wherein another end of the positioning sleeve has a grip configured to be held by a user.

4. The auxiliary surgical tool kit as recited in claim 1, wherein the sidewall of the through passage is further provided with a discharge opening.

5. The auxiliary surgical tool kit as recited in claim 1, wherein the shaping blade has a positioning protrusion.

6. The auxiliary surgical tool kit as recited in claim 1, further comprising a debridement drill configured to pass through the through passage of the positioning sleeve and remove a cartilage located at the to-be-implanted region of the patient.

7. The auxiliary surgical tool kit as recited in claim 6, wherein the debridement drill has a stopper, and the stopper has a size greater than a size of the through passage and is configured to limit a debridement depth of the debridement drill.

8. The auxiliary surgical tool kit as recited in claim 1, further comprising a drilling instrument configured to pass through the through passage of the positioning sleeve and drill a plurality of positioning holes in the cartilage located at the to-be-implanted region of the patient.

9. The auxiliary surgical tool kit as recited in claim 8, wherein the drilling instrument has a second alignment protrusion, and the second alignment protrusion is mutually aligned with the alignment groove.

10. A cartilage repair system, comprising:
    a cartilage repair implant, comprising a body and a plurality of pins, wherein the body is a porous structure and configured to carry a cartilage repair material, one end of each of the pins is fixed to the body, and another end of each of the pins is configured to insert into a bone of a patient;
    a positioning sleeve, having a through passage, wherein a alignment groove is disposed on a sidewall of the through passage; and
    a click tool, comprising an outer tube and a push rod, wherein a first alignment protrusion is disposed on an outer wall of the outer tube, the outer tube is configured to pass through the through passage of the positioning sleeve, and the first alignment protrusion is mutually aligned with the alignment groove, the push rod is slidably disposed in the outer tube, one end of the outer tube has a shaping blade configured to slice a to-be-implanted region on an affected area of the patient, and a shape of the to-be-implanted region is corresponding to a shape of the body.

11. The cartilage repair system as recited in claim 10, wherein a porosity of the porous structure ranges from 50% to 90%.

12. The cartilage repair system as recited in claim 10, wherein a periphery of the body has a positioning protrusion.

13. The cartilage repair system as recited in claim 10, wherein one end of the positioning sleeve has a plurality of sleeve pins configured to insert into the affected area of the patient.

14. The cartilage repair system as recited in claim 10, further comprising a debridement drill configured to pass through the through passage of the positioning sleeve and remove a cartilage located at the to-be-implanted region of the patient.

15. The cartilage repair system as recited in claim 10, further comprising a drilling instrument configured to pass through the through passage of the positioning sleeve and drill a plurality of positioning holes in the cartilage located at the to-be-implanted region of the patient, wherein the positioning holes are corresponding to the pins.

* * * * *